United States Patent
Wang et al.

(10) Patent No.: US 10,023,582 B2
(45) Date of Patent: Jul. 17, 2018

(54) 6-ARYL AMINO PYRIDONE FORMAMIDE COMPOUND CRYSTAL AND PREPARATION METHOD THEREFOR

(71) Applicants: Chia Tai Tianqing Pharmaceutical Group Co., Ltd., Lianyungang, Jiangsu Province (CN); Centaurus Biopharma Co., Ltd., Beijing (CN)

(72) Inventors: Lulu Wang, Lianyungang (CN); Xiquan Zhang, Lianyungang (CN); Fei Liu, Lianyungang (CN); Yizhong Zhu, Lianyungang (CN); Chao Gao, Lianyungang (CN); Song Tang, Lianyungang (CN); Bo Zhu, Lianyungang (CN); Jianqiu Tang, Lianyungang (CN)

(73) Assignees: Chia Tai Tianqing Pharmaceutical Group Co., Ltd., Lianyungang (CN); Centaurus Biopharma Co., Ltd., Bejing (CN)

( * ) Notice: Subject to any disclaimer, the term of this patent is extended or adjusted under 35 U.S.C. 154(b) by 0 days.

(21) Appl. No.: 15/329,197

(22) PCT Filed: Aug. 5, 2015

(86) PCT No.: PCT/CN2015/086118
§ 371 (c)(1),
(2) Date: Jan. 25, 2017

(87) PCT Pub. No.: WO2016/019867
PCT Pub. Date: Feb. 11, 2016

(65) Prior Publication Data
US 2017/0217979 A1    Aug. 3, 2017

(30) Foreign Application Priority Data
Aug. 5, 2014  (CN) .......................... 2014 1 0383541

(51) Int. Cl.
*C07D 491/048* (2006.01)

(52) U.S. Cl.
CPC ...... *C07D 491/048* (2013.01); *C07B 2200/13* (2013.01)

(58) Field of Classification Search
CPC .................................................. C07D 491/048
See application file for complete search history.

(56) References Cited

U.S. PATENT DOCUMENTS
2012/0238599 A1    9/2012  Lee et al.

FOREIGN PATENT DOCUMENTS
CN             102020651 A         4/2011

OTHER PUBLICATIONS

Zell et. al. "Investigation of Polymorphism in Aspartame and Neotame Using Solid-State NMR Spectroscopy." Tetrahedron 2000, 56 ,6603-6616.*
International Search Report in PCT/CN2015/086118, dated Nov. 24, 2015.

* cited by examiner

*Primary Examiner* — David K O'Dell
(74) *Attorney, Agent, or Firm* — Kilpatrick Townsend & Stockton LLP

(57) ABSTRACT

The present invention provides a crystal of 6-arylamino pyridone carboxamide compound and a preparation method thereof. The crystal is obtained by dissolving 6-(2-chloro-4-iodophenylamino)-N-(2-hydroxylethyoxyl)-5-methyl-4-oxo-4,5-dihydrofuro[3,2-c]pyridin-7-carboxamide in an aprotic polar solvent and adding a second solvent thereto. The crystallization method has the advantage of simple and convenient operations, and is beneficial to an industrial production. The resulting crystal has the advantage a high purity and good stability, and is benefit to the manufacture and storage of a medicament containing the same.

17 Claims, 1 Drawing Sheet

6-ARYL AMINO PYRIDONE FORMAMIDE COMPOUND CRYSTAL AND PREPARATION METHOD THEREFOR

TECHNICAL FIELD

The present invention relates to a crystal of 6-arylamino pyridone carboxamide compound and a preparation method thereof in the technical field of medicine.

CROSS REFERENCE TO RELATED APPLICATIONS

This application is a 371 U.S. National Phase of PCT/CN2015/086118, international filing date Aug. 5, 2015 which claims priority to Chinese Application No. 20141038354.7, filed Aug. 5, 2014, the contents of which are incorporated by reference in the entirety.

BACKGROUND ART

CN102020651A discloses a 5-arylamino pyridone carboxamide compound, whose chemical name is 6-(2-chloro-4-iodophenylamino)-N-(2-hydroxylethyoxyl)-5-methyl-4-oxo-4,5-dihydrofuro[3,2-c]pyridine-7-carboxamide, and the structural formula is represented by formula (I). The compound of formula (I) is a MEK inhibitor, which can be used in a method for treating MEK-mediated conditions or disorders in a mammal (including human), such as inflammatory diseases, infections, autoimmune diseases, strokes, ischemias, noncancerous hyperproliferative diseases, tumors and the like.

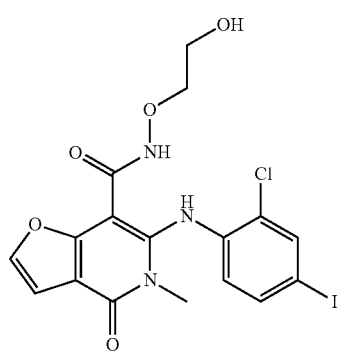

Formula (I)

CN102020651A discloses a preparation method of the compound of formula (I), which is obtained through a silica gel flash column chromatography. The morphology of a drug plays a crucial role in improving properties of the drug and obtaining a more desired processing performance. Accordingly a research on polymorph(s) of the compound of formula (I) has a great importance for its production.

SUMMARY OF THE INVENTION

The present invention provides a crystal of the compound of formula (I) characterized by diffraction peaks expressed by 2θ values at 7.86°, 19.09°, 21.80°, 23.87°, 26.00°, and 28.12° in an X-ray powder diffraction spectrum; typically, diffraction peaks expressed by 2θ values at 7.86°, 9.32°, 13.25°, 15.06°, 19.09°, 21.80°, 22.46°, 22.81°, 23.87°, 26.00°, 28.12°, and 28.59° in an X-ray powder diffraction spectrum; and more typically, diffraction peaks expressed by 2θ values at 7.86°, 9.32°, 13.25°, 15.06°, 17.89°, 19.09°, 20.73°, 21.80°, 22.46°, 22.81°, 23.87°, 24.55°, 26.00°, 27.29°, 28.12°, 28.59°, 29.32°, and 30.15° in an X-ray powder diffraction spectrum.

In one embodiment of the present invention, the crystal of the compound of formula (I) according to the present invention is characterized by an X-ray powder diffraction spectrum having the positions and intensities of diffraction peaks as shown in the following table.

| No. | Diffraction peak (°) | Relative intensity (%) |
| --- | --- | --- |
| 1 | 7.86 | 100 |
| 2 | 9.32 | 33 |
| 3 | 13.25 | 41 |
| 4 | 15.06 | 42 |
| 5 | 17.89 | 18 |
| 6 | 19.09 | 67 |
| 7 | 20.73 | 27 |
| 8 | 21.80 | 44 |
| 9 | 22.46 | 37 |
| 10 | 22.81 | 39 |
| 11 | 23.87 | 95 |
| 12 | 24.55 | 21 |
| 13 | 26.00 | 65 |
| 14 | 27.29 | 19 |
| 15 | 28.12 | 43 |
| 16 | 28.59 | 40 |
| 17 | 29.32 | 18 |
| 18 | 30.15 | 20 |

In one specific embodiment of the present invention, the crystal of the compound of formula (I) is characterized by an X-ray powder diffraction spectrum as shown in FIG. 1.

A typical but non-limited example of the crystal of the compound of formula (I) as provided by the present invention is characterized by a differential scanning calorimetry (DSC) thermogram having an absorption peak at about 202.2° C.

In one specific embodiment of the present invention, the crystal of the compound of formula (I) is characterized by a DSC thermogram as shown in FIG. 2.

In another aspect, the present invention provides a crystalline composition comprising the above crystal of the compound of formula (I) in an amount of 50% or more by weight of the crystalline composition, preferably 80% or more, more preferably 90% or more, and most preferably 95% or more.

In another aspect, the present invention provides a pharmaceutical composition comprising a therapeutically effective amount of the above crystal of the compound of formula (I) or the above crystalline composition.

In another aspect, the present invention provides a use of the above crystal of the compound of formula (I), the above crystalline composition or the above pharmaceutical composition in the preparation of a medicament for inhibiting MEK enzyme.

In another aspect, the present invention provides a use of the above crystal of the compound of formula (I), the above crystalline composition or the above pharmaceutical composition in the preparation of a medicament for treating or preventing MEK-mediated disorders or diseases. Preferably, the MEK-mediated disorders or diseases are MEK-mediated proliferative diseases. Preferably, the MEK-mediated proliferative diseases are inflammatory diseases or cancers.

In another aspect, the present invention provides a method for preparing the above crystal of the compound of formula (I) or the above crystalline composition, comprising the following steps: dissolving a crude compound of formula (I)

in an aprotic polar solvent at a temperature of 80° C.-120° C.; lowering the temperature; adding a second solvent; crystallizing; filtrating and drying.

In the above steps, the aprotic polar solvent can be selected from the group consisting of DMF, DMSO and a mixed solvent thereof, preferably DMSO.

In the above steps, the second solvent is selected from the group consisting of water, alcohols and a mixed solvent thereof, preferably water, methanol, ethanol, n-propanol, isopropanol, n-butanol, isobutanol or a mixture of two or more of the above solvents, further preferably ethanol, water or a mixture of water and ethanol, and still further preferably ethanol.

In the above steps, a ratio of a mass of the crude compound of formula (I) to a volume of the aprotic polar solvent is 10 g:5 mL-10 g:25 mL, preferably 10 g:10 mL-10 g:20 mL, and still further preferably 10 g:10 mL-10 g:15 mL.

In the above steps, a temperature of the aprotic polar solvent is preferably 90° C.-110° C., and further preferably 100° C.-110° C.

In the above steps, a volume ratio of the second solvent to the aprotic polar solvent is 0.25:1-5:1, preferably 0.5:1-3:1, and still further preferably 1:1-2:1.

In the above steps, the temperature can be lowered to 30° C.-50° C., preferably 35° C.-45° C. The step of lowering the temperature may be carried out by natural cooling.

In the above steps, the drying step is preferably performed under a reduced pressure, and still further preferably in vacuum at a temperature of 40° C.

In the above steps, the crude compound of formula (I) is dissolved in the aprotic polar solvent at a temperature of 80° C.-120° C. The crude compound of formula (I) may be firstly mixed with the aprotic polar solvent, and then heated to a temperature of 80° C.-120° C. Alternatively, the aprotic polar solvent may be firstly heated to a temperature of 80° C.-120° C., and then mixed with the crude compound of formula (I).

In the present invention, the crude compound of formula (I) may be obtained through a preparation method described in CN102020651A or in the examples of the present invention.

In the present invention, DMF refers to N, N-dimethylformamide, and DMSO refers to dimethyl sulfoxide.

In the present invention, according to the Chinese Pharmacopoeia, 2010 edition, Appendix VIII Q, DSC thermogram is measured under the following conditions: detector: Mettler Toledo DSCl; measuring condition: heating from 80° C. to 300° C. at a rate of 10° C./min; environmental condition of detection: a room temperature of 21° C. and a humidity of 50%.

It should be noticed that in an X-ray powder diffraction spectrum (XRD) a diffraction pattern of a crystalline compound is frequently characteristic for a specific crystalline form. Relative intensities of the bands (especially at the low angle) can vary depending upon preferential orientation effects resulting from the crystallization conditions, particle size, and different measuring conditions. Therefore, relative intensities of diffraction peaks are not characteristic for a specific crystalline form. It is the relative position of peaks rather than relative intensities thereof that should be paid more attention when judging whether a crystalline form is the same as the known crystalline form. In additional, as for any given crystal, there may be a slight error in the position of a peak, which is also well known in the field of crystallography. For example, the position of a peak may shift due to the change of a temperature, the movement of a sample or the calibration of an instrument and so on when analyzing the sample, and the measurement error of 2θ value sometimes is about ±0.2°. Accordingly, this error should be taken into consideration when identifying a crystal structure. Usually, the position of a peak is expressed in terms of 2θ angle or lattice spacing d in XRD spectrum and the simple conversion relationship therebetween is d=λ/2 sin θ, wherein d represents the lattice spacing, λ represents the wavelength of incident X-ray, and θ represents the diffraction angle. For the same crystalline form of the same compound, the position of a peak in XRD spectrum thereof has similarity on the whole, and accordingly the error of a relative intensity may be relatively large. In addition, it is necessary to point out that due to some factors such as reduced contents, parts of diffraction lines may be absent in identification of a mixture. At this time, even a band may be characteristic for the given crystalline form without depending upon the whole bands of a high purity sample.

DSC is used to measure a thermal transition temperature when absorbing or releasing heat due to the change of a crystal structure or the melting of a crystal. In a continuous analysis of the same crystalline form of the same compound, the error of a thermal transition temperature and a melting point is typically within a range of about ±5° C. generally within a range of about ±3° C. A compound with a given DSC peak or melting point means that the DSC peak or melting point may be varied within a range of ±5° C. DSC provides an auxiliary method to distinguish different crystalline forms. Different crystalline forms can be identified by their characteristically different transition temperatures. It is necessary to point out that the DSC peak or melting point of a mixture will vary over a wider range. Furthermore, because of the decomposition in the melting process, the melting temperature is closely related to a heating rate.

The crystal of the compound of formula (I) provided by the present invention has some advantages, such as high purity and good stability, and is beneficial to the manufacture and storage of a medicament containing the same. The preparation method of the crystal of the compound of formula (I) provided by the present invention has the advantage of simple and convenient operations, and is beneficial to its industrial production.

DETAILED DESCRIPTION OF PREFERRED EMBODIMENTS

Figure 1:
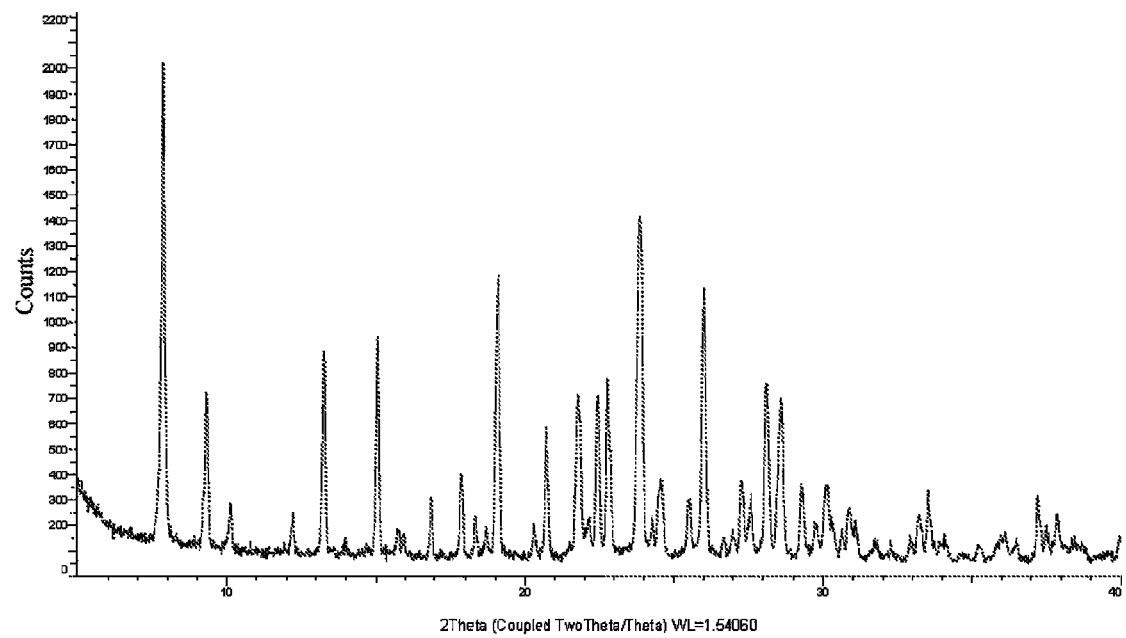
FIG. 1 shows X-ray powder diffraction spectrum of the crystal of the compound of formula (I) in Example 4.
Figure 2:
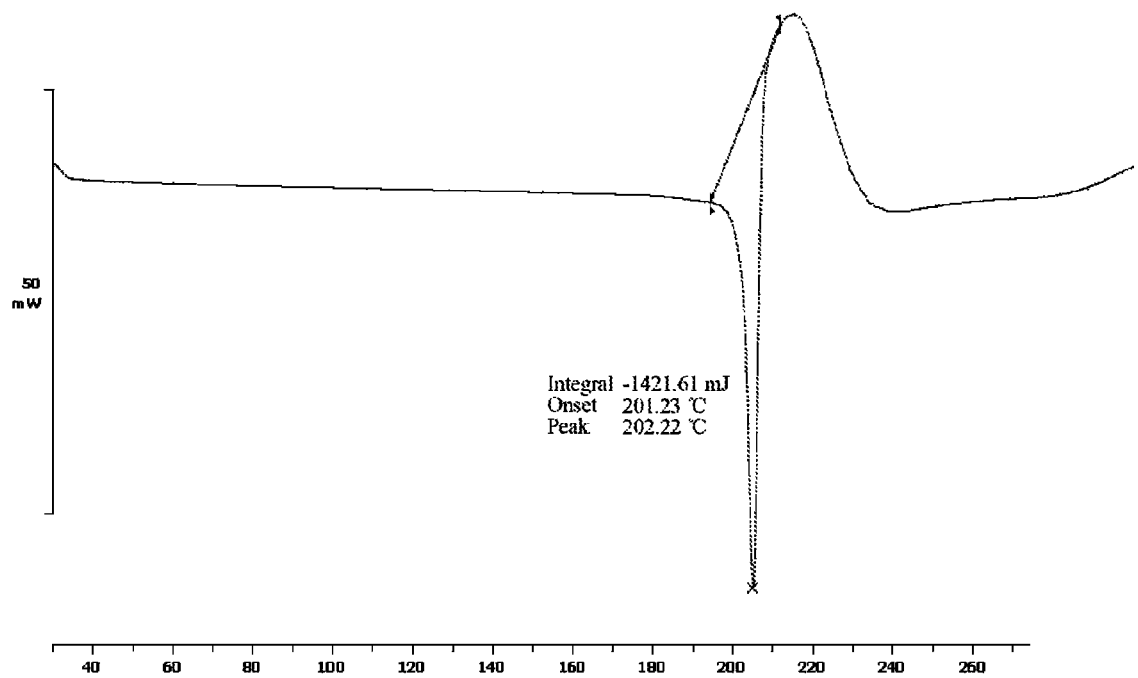
FIG. 2 shows DSC thermogram of the crystal of the compound of formula (I) in Example 4.

The following specific: examples illustrate the technical solutions of the present invention, but the scope of the present invention is not limited to the scope of the examples described herein. Reagents used in the examples are commercially available.

Example 1 Preparation of the Crude Compound of Formula (I)

5 g of compound 6-(2-chloro-4-iodophenylamino)-N-(2-ethenyloxyethoxyl)-5-methyl-4-oxo-4,5-dihydrofuro[3,2-c]pyridine-7-carboxamide was weighed and dissolved in 50 mL of anhydrous tetrahydrofuran at room temperature. The reaction temperature was lowered to −10° C., and then about 20 mL of 6 N HCl was slowly added dropwise. After completion of the addition, the reaction was maintained at a temperature of 5-10° C. for about 2 h. After completion of the reaction, the reaction mixture was poured into an ice water, and extracted with ethyl acetate. The organic solvents were removed by evaporation. The resulting solid was slurred with ethanol, and filtrated to obtain a pale yellow solid.

Example 2 Preparation of the Crystal of the Compound of Formula (I)

10 g of the crude compound of formula (I) prepared in Example 1 was weighed and added to 5 mL of DMSO. The temperature was raised to about 110° C. such that the compound was dissolved to obtain a clear solution, and then it was naturally cooled down. 25 ml of water was added thereto when the temperature was cooled to 45° C., and stirring was continued. A large amount of off-white solid was precipitated out, filtrated and dried at a temperature of 50° C. in vacuum to obtain a white or off-white crystal.

Example 3 Preparation of the Crystal of the Compound of Formula (I)

10 g of the crude compound of formula (I) prepared in Example 1 was weighed and added to 10 mL of DMF. The temperature was raised to about 100° C. such that the compound was dissolved to obtain a clear solution, and then it was naturally cooled down. 30 ml of isopropanol was added thereto when the temperature was cooled to 45° C., and stirring was continued. A large amount of off-white solid was precipitated out, filtrated and dried at a temperature of 50° C. in vacuum to obtain a white or off-white crystal.

Example 4 Preparation of the Crystal of the Compound of Formula (I)

10 g of the crude compound of formula (I) prepared in Example 1 was weighed and added to 10 mL, of DMSO. The temperature was raised to about 100° C. such that the compound was dissolved to obtain a clear solution, and then it was naturally cooled down. 15 ml of ethanol was added thereto when the temperature was cooled to 50° C., and stirring was continued. A large amount of off-white solid was precipitated out, filtrated and dried at a temperature of 50° C. in vacuum to obtain a white or off-white crystal.

Example 5 Preparation of the Crystal of the Compound of Formula (I)

10 g of the crude compound of formula (I) prepared in Example 1 was weighed and added to 10 mL DMSO. The temperature was raised to about 120° C. such that the compound was dissolved to obtain a clear solution, and then it was naturally cooled down. 20 ml of methanol was added thereto when the temperature was cooled to 50° C., and stirring was continued. A large amount of off-white solid was precipitated out, filtrated and dried at a temperature of 50° C. in vacuum to obtain a white or off-white crystal.

Example 6 Preparation of the Crystal of the Compound of Formula (I)

10 g of the crude compound of formula (I) prepared in Example 1 was weighed and added to 15 mL of DMSO. The temperature was raised to about 110° C. such that the compound was dissolved to obtain a clear solution, and then it was naturally cooled down. 15 ml of water was added thereto when the temperature was cooled to 60° C., and stirring was continued. A large amount of off-white solid was precipitated out, filtrated and dried at a temperature of 50° C. in vacuum to obtain a white or off-white crystal.

Example 7 Preparation of the Crystal of the Compound of Formula (I)

10 g of the crude compound of formula (I) prepared in Example 1 was weighed and added to 20 mL of DMF. The temperature was raised to about 90° C. such that the compound was dissolved to obtain a clear solution, and then it was naturally cooled down. 5 ml of ethanol was added thereto when the temperature was cooled to 30° C., and stirring was continued. A large amount of off-white solid was precipitated out, filtrated and dried at a temperature of 50° C. in vacuum to obtain a white or off-white crystal.

Example 8 Preparation of the Crystal of the Compound of Formula (I)

10 g of the crude compound of formula (I) prepared in Example 1 was weighed and added to 25 mL of DMF. The temperature was raised to about 80° C. such that the compound was dissolved to obtain a clear solution, and then it was naturally cooled down. 12.5 ml of methanol was added thereto when the temperature was cooled to 35° C., and stirring was continued. A large amount of off-white solid was precipitated out, filtrated and dried at a temperature of 50° C. in vacuum to obtain a white or off-white crystal.

Example 9 Purity Determination of the Crystal of the Compound of Formula (I)

The purity of the crystal of the compound of formula (I) was measured by high performance liquid chromatography according to the Chinese Pharmacopoeia, 2010 edition, Part II, Appendix V D. Ostade-cylsilane (ODS) was used as a filler [Recommended column: Eclipse XDB-C18 (4.6×150 mm, 5 µm) or other chromatographic columns having a comparable performance]; water (0.01% trifluoroacetic acid solution) was used as mobile phase A; acetonitrile (0.01% trifluoroacetic acid solution) was used as mobile phase B; the flow rate was 1.0 ml/min with the linear gradient elution as shown in Table 1; the column temperature was 30° C.; the detection wavelength was 244 nm; and the theoretical plate number was no less than 2000 upon calculation based on the compound of formula (I).

TABLE 1

Measurement conditions of HPLC

| Time (min) | Mobile phase A (%) | Mobile phase B (%) |
|---|---|---|
| 0 | 80 | 20 |
| 8 | 40 | 60 |
| 11 | 10 | 90 |
| 12 | 80 | 20 |
| 20 | 80 | 20 |

A suitable amount of the crystal of the compound of formula (I) prepared in Example 4 was accurately weighed, and methanol was then added thereto to dissolve the crystal. It was diluted quantitatively to obtain a solution containing about 50 µg of the compound per 1 ml of the solution. 10 µl of the solution was accurately measured and injected into the liquid chromatograph, and the chromatogram was recorded. In addition, a suitable amount of the compound of formula (I) was weighed as a control, and measured by the same method as described in the above. The purity was calculated through external standard method based on peak areas.

The purity of the crystal of the compound of formula (I) prepared in Example 4 was 99.4% as determined by HPLC.

Example 10 Stability Test

Referring to the test method of influencing factors for raw materials described in the Chinese Pharmacopoeia, 2010 edition, Part II, Appendix XIX C, a high-temperature experiment (40° C.±2° C. and a relative humidity of 75%±5%) and strong light irradiation experiment (4500lx±500lx) were conducted on the crystal of the compound of formula (I) prepared in Example 4 for 10 days, respectively. Samples were taken on day 0 and day 10 to measure a total amount of impurities and determine the stability. The test results were shown in Table 2.

TABLE 2

Stability test results

| Testing item | | The crystal of the compound of formula (I) in Example 4 |
|---|---|---|
| Total amount of impurities (%) | Day 0 | 0.57 |
| | Irradiation for 10 days | 0.68 |
| | At 40° C., 10 days | 0.60 |

What is claimed is:

1. A crystal of a compound of formula (I) characterized by diffraction peaks expressed by 2θ values at 7.86°, 19.09°, 21.80°, 23.87°, 26.00°, and 28.12° in an X-ray powder diffraction spectrum,

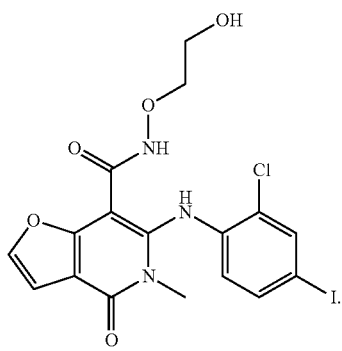

(I)

2. The crystal of claim 1, which is characterized by diffraction peaks expressed by 2θ values at 7.86°, 9.32°, 13.25°, 15.06°, 19.09°, 21.80°, 22.46°, 22.81°, 23.87°, 26.00°, 28.12°, and 28.59° in the X-ray powder diffraction spectrum.

3. The crystal of claim 2, which is characterized by diffraction peaks expressed by 2θ values at 7.86°, 9.32°, 13.25°, 15.06°, 17.89°, 19.09°, 20.73°, 21.80°, 22.46°, 22.81°, 23.87°, 24.55°, 26.00°, 27.29°, 28.12°, 28.59°, 29.32°, and 30.15° in the X-ray powder diffraction spectrum.

4. A crystalline composition, comprising the crystal of the compound of formula (I) of claim 1 in an amount of 50% or more by weight of the crystalline composition.

5. A pharmaceutical composition, comprising a therapeutically effective amount of the crystal of claim 1.

6. A method for preparing a crystal of a compound of formula (I) of claim 1 or a crystalline composition thereof, comprising the following steps: dissolving a crude compound of formula (I) in an aprotic polar solvent at a temperature of 80° C.-120° C., lowering the temperature, adding a second solvent, crystallizing, filtrating and drying.

7. The method of claim 6, wherein the aprotic polar solvent is selected from the group consisting of DMF, DMSO and a mixed solvent thereof.

8. The method of claim 6, wherein the second solvent is selected from the group consisting of water, alcohols and a mixed solvent thereof.

9. The method of claim 6, wherein a volume ratio of the second solvent to the aprotic polar solvent is 0.25:1-5:1.

10. A crystalline composition, comprising the crystal of the compound of formula (I) of claim 1 in an amount of 80% or more by weight of the crystalline composition.

11. A crystalline composition, comprising the crystal of the compound of formula (I) of claim 1 in an amount of 90% or more by weight of the crystalline composition.

12. A crystalline composition, comprising the crystal of the compound of formula (I) of claim 1 in an amount of 95% or more by weight of the crystalline composition.

13. The method of claim 7, wherein the aprotic polar solvent is DMSO.

14. The method of claim 8, wherein the second solvent is selected from the group consisting of water, methanol, ethanol, n-propanol, isopropanol, n-butanol, isobutanol, and a mixture of two or more of the above solvents.

15. The method of claim 8, wherein the second solvent is selected from the group consisting of ethanol, water, and a mixture of ethanol and water.

16. The method of claim 9, wherein a volume ratio of the second solvent to the aprotic polar solvent is 0.5:1-3:1.

17. The method of claim 9, wherein a volume ratio of the second solvent to the aprotic polar solvent is 1:1-2:1.

* * * * *